United States Patent
Borut et al.

(10) Patent No.: US 6,644,507 B2
(45) Date of Patent: Nov. 11, 2003

(54) AUTOMATIC AIR FRESHENER WITH DYNAMICALLY VARIABLE DISPENSING INTERVAL

(75) Inventors: Severine N. Borut, Milwaukee, WI (US); Jayant Sharma, Racine, WI (US); Curtis H. Hubmann, Racine, WI (US); Patrick J. Prayne, Seneca Falls, NY (US)

(73) Assignee: JohnsonDiversey, Inc., Sturtevant, WI (US)

( * ) Notice: Subject to any disclaimer, the term of this patent is extended or adjusted under 35 U.S.C. 154(b) by 0 days.

(21) Appl. No.: 10/097,879

(22) Filed: Mar. 14, 2002

(65) Prior Publication Data

US 2002/0130146 A1 Sep. 19, 2002

Related U.S. Application Data

(60) Provisional application No. 60/275,831, filed on Mar. 14, 2001.

(51) Int. Cl.$^7$ ................................. B65H 3/00
(52) U.S. Cl. ........................ 222/37; 222/38; 222/63; 222/646; 222/649
(58) Field of Search ....................... 222/23, 36, 37, 222/38, 63, 645, 646, 647, 648, 649

(56) References Cited

U.S. PATENT DOCUMENTS

| | | | |
|---|---|---|---|
| 3,779,425 A | 12/1973 | Werner | 222/70 |
| 3,952,916 A | 4/1976 | Phillips | 222/70 |
| 4,063,664 A | 12/1977 | Meetze, Jr. | 222/70 |
| 4,483,466 A * | 11/1984 | Gutierrez | 222/647 |
| 4,671,435 A | 6/1987 | Stout et al. | 222/646 |
| 4,719,851 A | 1/1988 | Chesnut | 100/45 |
| 4,830,791 A | 5/1989 | Muderlak et al. | 261/26 |
| 5,038,972 A | 8/1991 | Muderlak et al. | 222/25 |
| D323,884 S | 2/1992 | Muderlak | D23/366 |
| D325,253 S | 4/1992 | Muderlak | D23/366 |
| 5,111,477 A | 5/1992 | Muderlak | 392/390 |
| D330,758 S | 11/1992 | Muderlak | D23/366 |
| 5,175,791 A | 12/1992 | Muderlak et al. | 392/390 |
| D338,522 S | 8/1993 | Muderlak | D23/366 |
| 5,249,718 A | 10/1993 | Muderlak | 222/642 |
| 5,358,147 A | 10/1994 | Adams et al. | 222/183 |
| RE34,847 E | 2/1995 | Muderlak et al. | 222/25 |
| D357,977 S | 5/1995 | Muderlak | D23/366 |
| 5,449,117 A | 9/1995 | Muderlak et al. | 239/6 |
| D363,981 S | 11/1995 | Muderlak | D23/366 |
| D366,520 S | 1/1996 | Muderlak | D23/366 |
| D370,057 S | 5/1996 | Muderlak | D23/309 |
| 5,673,825 A | 10/1997 | Chen | 222/646 |
| 5,680,879 A | 10/1997 | Sheih et al. | 137/240 |
| D393,706 S | 4/1998 | Kauzlarich et al. | D23/369 |
| 5,772,074 A | 6/1998 | Dial et al. | 222/1 |
| 5,823,390 A | 10/1998 | Muderlak et al. | 222/38 |
| 5,884,808 A | 3/1999 | Muderlak et al. | 222/23 |
| 5,908,140 A | 6/1999 | Muderlak et al. | 222/1 |
| 5,938,076 A | 8/1999 | Ganzeboom | 222/23 |
| 6,036,108 A | 3/2000 | Chen | 239/274 |
| 6,039,212 A | 3/2000 | Singh | 222/30 |
| 6,182,904 B1 | 2/2001 | Ulczynski et al. | 239/1 |
| 6,394,310 B1 * | 5/2002 | Muderlak et al. | 222/1 |

FOREIGN PATENT DOCUMENTS

| | | | |
|---|---|---|---|
| WO | WO96/30726 | 10/1996 | |
| WO | 97/13086 | 4/1997 | 31/2 |
| WO | 97/13088 | 4/1997 | 31/10 |

* cited by examiner

*Primary Examiner*—Joseph A. Kaufman
(74) *Attorney, Agent, or Firm*—Neil E. Hamilton; Warren R. Bovee; Renee J. Rymarz

(57) ABSTRACT

An apparatus periodically dispenses an air freshening substance from a pressurized container into a room. A device is provided to sense when the room is occupied, such as by detecting the light level in the room. The air freshening substance is dispensed more frequently when the room is being used than at other times. However, the dispensing continues even when the room is unoccupied to treat odors arising from objects permanently located in the room.

16 Claims, 3 Drawing Sheets

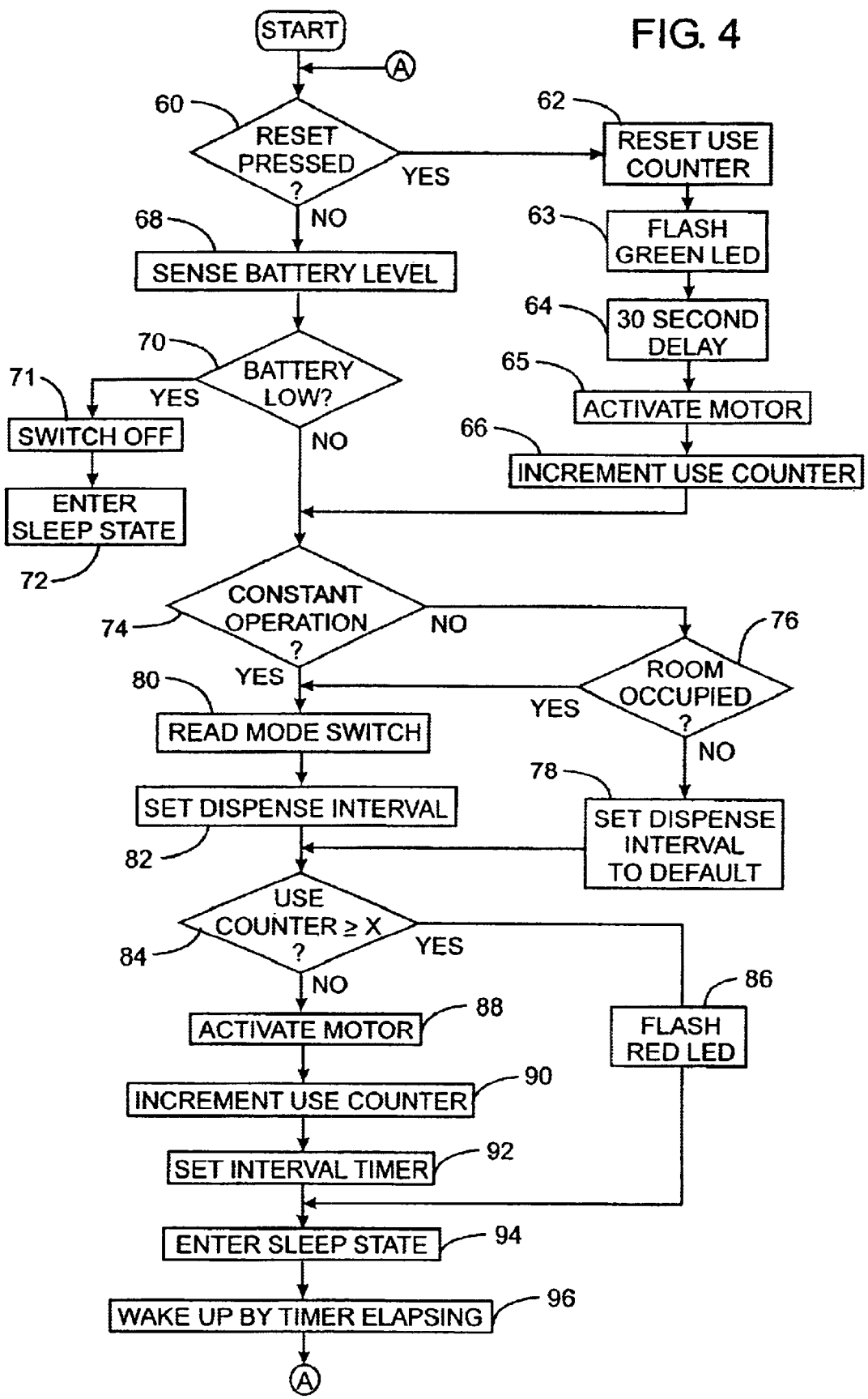

AUTOMATIC AIR FRESHENER WITH DYNAMICALLY VARIABLE DISPENSING INTERVAL

CROSS REFERENCE TO RELATED APPLICATIONS

This is a formal application which claims priority of Provisional Patent Application No. 60/275,831, filed Mar. 14, 2001.

STATEMENT REGARDING FEDERALLY SPONSORED RESEARCH OR DEVELOPMENT

None

BACKGROUND OF THE INVENTION

The present invention relates to aerosol air fresheners, and more particularly to apparatus for automatically dispensing an air freshening substance at controlled intervals.

Air fresheners are commonly used to mask odors within bathrooms and other interior spaces. The air freshening substance may also chemically neutralize the odors. Devices have been developed to automatically dispense the air freshening substance.

One common type of dispenser utilizes a scented liquid contained in a pressurized canister. The canister is mounted in a holder which includes a motor that periodically operates a valve on the canister to dispense the scented liquid into the environment. The motor is periodically activated by a timer. The timing period typically is fixed and cannot be varied to meet the needs of a particular room in which the dispenser is installed. As a consequence, a greater amount of scented liquid may be dispensed into a room with a mild odor problem, and an insufficient amount of the scented liquid may be dispensed in a room with more persistent odors.

Furthermore, once installed and activated, the device dispenses the scented liquid at regular intervals until the air freshener becomes depleted. Thus if the room is not occupied for a long period of time, during which air freshening is not required, the scented liquid continues to be dispensed at the same rate as when the room is occupied. It is desirable to control the dispensing in relation to the occupancy or usage of the room in which the dispenser is located.

It is also desirable to provide a mechanism which indicates to the user when the supply of scented liquid in the canister becomes depleted. Otherwise the user has to periodically open the dispenser housing and inspect the canister to determine depletion of the air freshening substance therein.

SUMMARY OF THE INVENTION

An apparatus periodically discharges a quantity of the contents of a canister, for example an air freshening substance, into a room. The apparatus has a motor which drives a member that engages the canister to open a valve thereby allowing the contents of the canister to be discharged.

A sensor responds to a characteristic of the room and produces a signal indicating that characteristic. The characteristic provides an indication of occupancy or usage of the room. In the preferred embodiment of the present apparatus, the sensor detects the magnitude of light within the room.

A control circuit is connected to the sensor and the motor. An input device is provided which enables a user to designate a dispense interval specifying the frequency at which the contents of the canister are to be discharged into a room. The control circuit evaluates the signal from the sensor to determine whether the room is being used. For example if the magnitude of light within the room exceeds a threshold level, as occurs when the room lighting is on, a controller determines that the room is in use and occupied. The controller periodically activates the motor at intervals which correspond to the selected dispense interval when a determination is made that the room is being used, and at other times the controller periodically activates the motor at intervals which are longer than the dispense interval.

Thus the contents of the canister are dispensed more frequently when the room is in use, than when it is unoccupied. Therefore, the contents of the canister are conserved for periods of room usage while still providing a degree of dispensing at other times.

BRIEF DESCRIPTION OF THE DRAWINGS

FIG. 4 is a flow chart depicting operation of the control circuitry.

DETAILED DESCRIPTION OF THE INVENTION

Figure 1:
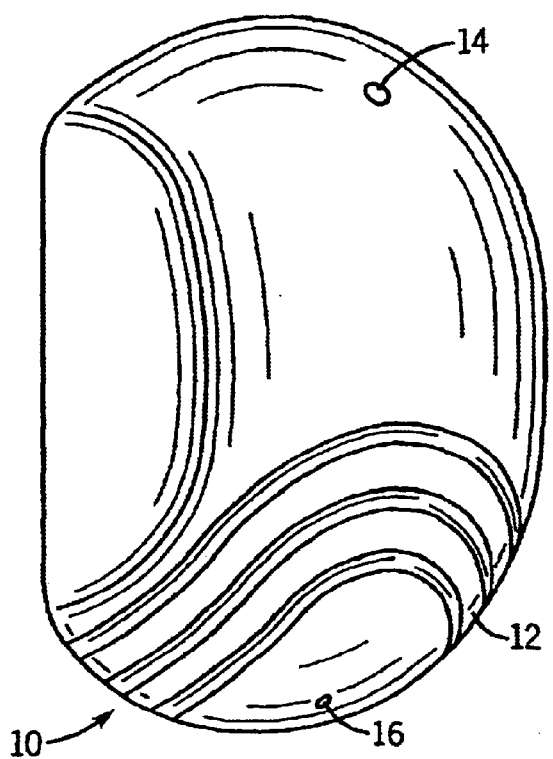
FIG. 1 is an isometric view of an exemplary air freshener according to the present invention.

With initial reference to FIG. 1, an automatic air freshener dispenser 10 has a housing 12 with a flat rear cover that mounts against the wall of the room. The housing has a first aperture 14 through which an aerosol air freshening substance is dispensed and has a second aperture in which an indicator, such as a light emitting diode (LED) 16, is mounted.

Figure 2:
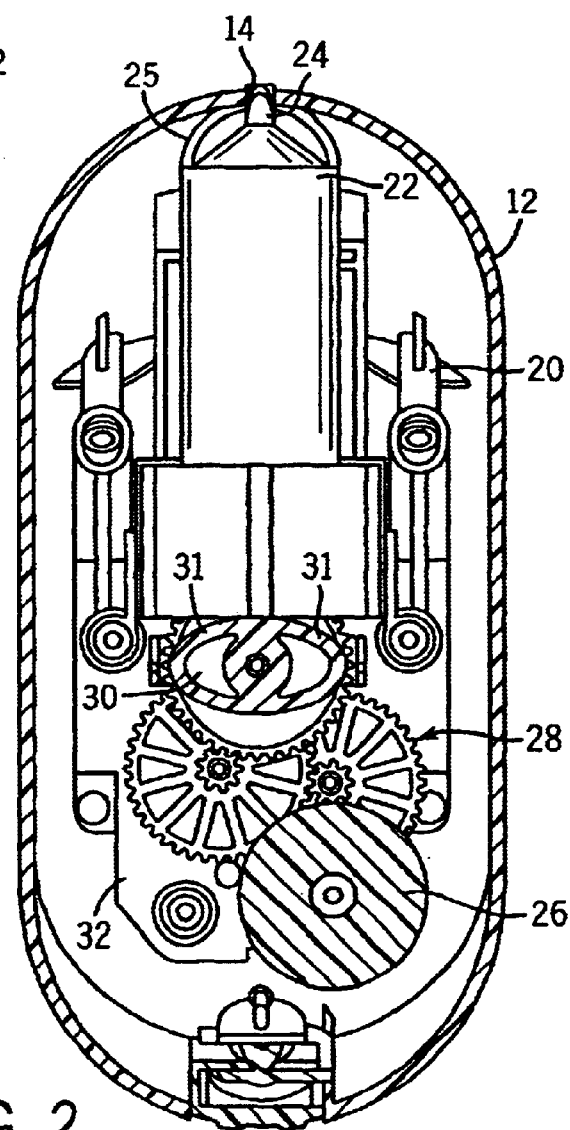
FIG. 2 illustrates the interior of the air freshener.

FIG. 2 illustrates the components which are mounted on a frame 20 inside the housing 12. A pressurized canister 22 of an air freshener liquid is removably received in the frame 20 and has an outlet nozzle 24 with an integral valve that extends into the first aperture 14 in the housing. The canister 22 is able to slide within the frame 20 toward and away from the first aperture, as will be described. FIG. 2 shows the normal, or non-dispensing, state of the air freshener dispenser.

An electric motor 26 also is mounted on the frame 20 and has an output shaft that engages a plurality of gears 28 which couple the motor to an actuator cam 30. The combination of the motor, the gears and the actuator cam form an actuator that engages the canister to open the valve. The motor 26 is electrically connected to a printed circuit board 32 attached to the frame 20 and receives power from one or more batteries (not visible) within the housing 12. As will be described, when the motor 26 is energized, the plurality of gears rotationally drive the actuator cam 30 so that one of the lobes 31 on the cam presses against the interior end of the canister 22. This causes the canister to slide within the frame 20 toward the first housing aperture 14 which compresses a bow spring 25 on the canister. As the canister 22 is pushed farther toward the first aperture 14 the valve of the outlet nozzle opens dispensing the freshening substance through the first aperture 14 in the housing 12.

With continued movement of the motor, the cam lobe 31 disengages from the end of the canister 12 allowing the canister to slide away from the first aperture 14 due to force from the compressed bow-spring 25. This motion closes the valve of the outlet nozzle thereby terminating the emission of the air freshening substance. The control circuit on the printed circuit board 32 energizes the motor 26 for an interval of time that is sufficient for the actuator cam 30 to make one-half a revolution, resulting in one air freshener dispensing cycle.

Figure 3:
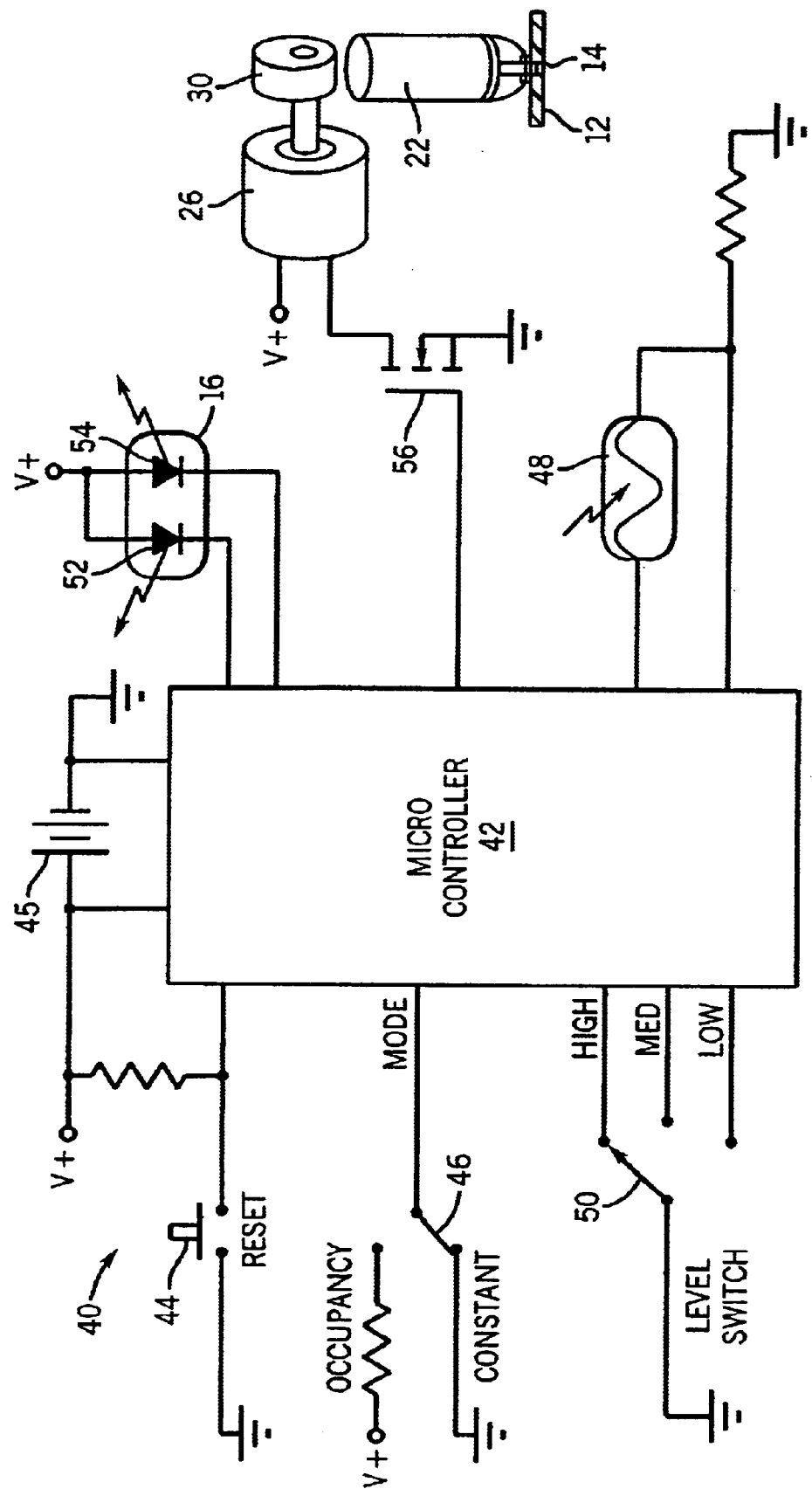
FIG. 3 is a schematic diagram of the control circuitry for the air freshener.

FIG. 3 illustrates the control circuit 40 which is mounted on printed circuit board 32. A controller 42, such as a conventional microcontroller, includes a microprocessor which executes a program stored in an internal memory. The memory also provides storage locations for data required by the air freshener operation. The controller 42 has input/output circuits for interfacing to external components of the control circuit 40. As an alternative to a programmable controller, the control circuit 40 can be implemented by a custom integrated circuit that has logic circuitry for controlling operation of the air freshener.

The controller 42 has a reset input connected to a reset switch 44 which when closed initializes execution of the control program. Other terminals of the controller 42 are connected to a light sensor 48 which produces an input signal indicative of the intensity of the ambient light within the room in which the air freshener dispenser 10 is located. This provides an occupancy sensing mechanism that denotes whether the room, such as a rest room, is being used and thus requires relatively frequent air freshening. That is, the controller 42 determines that the room is being used when the lights of the room are on, and determines that the room is not being used, or vacant, when the room lights are turned off.

Other room usage sensing mechanisms can be utilized with the present control circuit 40. For example, in the case of a bathroom, a switch can be mounted on the frame of the door into the room to provide an electrical signal each time the door is opened. The controller 42 can be programmed to measure the intervals between opening of the door and reach a conclusion that the room is not being actively used when the door has not been opened for a reasonably long period of time. A passive infrared radiation detector also can be used to sense the presence of people in the room.

The controller 42 has an input connected to a mode selector 46 that determines whether the air freshening substance is dispensed constantly at the same interval or operates in a mode in which the level of light sensed by light sensor 48 determines the interval at which the air freshening substance is dispensed, as will be described. Three other controller inputs are connected to level switch 50 which has three positions that allow the user to select from among three different intervals that specify the frequency at which the air freshening substance is to be dispensed. For example, the three positions of the level switch can select among dispensing the air freshening substance once an hour, once every two hours, or once every three hours. Other intervals can be employed depending upon the potency of the air freshening substance.

The controller 42 has outputs for driving the light emitting diode 16. The preferred embodiment of the present invention utilizes a dual light emitting diode 16 formed with two diodes 52 and 54, which are driven separately to emit red or green light, respectively. Another output of controller 42 is connected to the gate of a field effect transistor (FET) 56 that controls the application of electricity to the motor 26.

When the air freshener dispenser 10 is placed into use, a rear cover of the housing 12 is attached to a wall or other surface in a room. Such attachment may be by screws, an adhesive strip, or other suitable means. The user then inserts the batteries 45 (FIG. 3) into the dispenser, places a canister 22, containing the scented material, into the frame 20, and presses the reset button 44. The reset button 44 is pressed each time the canister 22 is replaced and signals the controller that a new supply of air freshening substance has been inserted into the dispenser.

The controller 42 executes a control program which is depicted by the flow chart in FIG. 4. The program commences at step 60, where a determination is made whether the reset switch 44 has been pressed by the user. If that is the case, the program execution branches to step 62 where a software implemented use counter is reset to zero. This counter maintains a count of the number of dispensing cycles that occur and the count, which is stored in the controller memory, is reset when a new canister 22 of scented material is inserted into the dispenser. At step 63, a routine is activated which periodically flashes the green LED 54 to provide an indication to the user that the dispenser is operating. Then at step 64, the program execution delays for thirty seconds to allow the user to close the housing 12. This delay prevents the user from being sprayed with air freshening substance. Upon the end of that delay, the motor 26 is activated at step 65 to spray the scented material from the canister 22 and demonstrate to the user that the dispenser 10 is operational. The use counter is incremented at step 66 to count the dispensing operation that just occurred. The program execution then jumps to step 74.

When the dispenser 10 is not found to have been reset at step 60, the control program branches to step 68 at which the controller 42 senses the voltage level from the batteries 45 and determines whether the batteries are becoming depleted at step 70. If the batteries are supplying a low voltage level, the dispenser is switched off at step 71 and then enters a sleep state at step 72. The controller will wake-up from this sleep state when the reset switch 44 is pressed as happens after the batteries are replaced.

When the voltage level is satisfactory, the program execution branches to step 74, the input connected to mode selector 46 is read by the controller 42 to determine whether the dispenser is to operate in the constant mode or the usage based mode. The position of the mode selector 46 is indicated by the voltage level at that input. As noted previously, the usage based operation utilizes the light sensor 48 to determine whether the room is being used as indicated by the light level within the room. In that operating mode, the control program branches to step 76 at which the input from the light sensor 48 is read and compared to a predefined threshold level that designates a sufficient magnitude of light to conclude that the room is being used by people. For example, the lights in a rest room are turned off during periods when a building is unoccupied and frequent air freshening is not required.

If the light level in the room is below the predefined threshold, the dispense interval is set at step 78 to a relatively long default period, for example four hours. This results in the dispenser emitting the air freshening substance once every four hours, so that some level of air freshening is maintained even during periods when the room is not occupied. As often is the case, odors can be emitted from objects that are in the room even when people are not present. The value determined for the dispense interval is stored in a designated location within the memory of the controller 42.

When either the switch 46 indicates the constant mode (i.e. dispenser operation regardless of room usage) or the room is determined to be in use in response to the light sensor at step 76, the program execution reaches step 80. At this juncture, the three inputs from the level switch 50 are read by the controller 42 to determine whether the dispenser is configured for the high, medium or low level of air freshening. As noted previously, each of these three levels of air freshening specify different frequencies at which the scented material is to be dispensed from the canister 22. Therefore, at step 82, the position of the level switch 50 is used to set the dispense interval which then is stored in memory. For example, the high setting may indicate that dispensing should occur once every hour, the medium setting once every two hours, and once every three hours for the low level setting.

After the dispense interval has been defined at either step 78 or 82 in FIG. 4, the program execution advances to step 84 where the value of the use counter is read and compared to a predefined value, designated "X", which corresponds to the number of dispensing cycles that can be obtained from the quantity of air freshening substance within the canister 22. This number of dispensing cycles is dependent upon the volume of the canister 22 and the amount of air freshening substance that is dispensed during each operating cycle of the dispenser 10. If the maximum number of dispensing cycles has occurred, the controller activates a routine which periodically flashes the red LED 52 at step 86. This provides a visual indication to the user that the air freshening substance within canister 22 has become exhausted and that a new canister should be inserted into the dispenser 10. The program then jumps to step 94 and enters the sleep state, bypassing the dispensing steps.

While the value of the use counter is less than the predefined value "X", the program execution branches to step 88 where the controller 42 turns on the FET 56 to activate the motor 26 for a predetermined period of time that is required to rotate actuator cam 30 one-half a revolution. The motion of the actuator cam 30 causes one of the lobes 31 to engage the inner end of the canister 22 and slide the canister toward the first aperture 14 compressing the bow spring 25. This action also pushes the outlet nozzle 24 into the canister thereby opening the valve and dispensing air freshening substance into the room.

As the actuator cam 30 continues to rotate, the lobe 31 moves past the end of the canister 22 allowing the force of the bow spring 25 to push the canister away from the first housing aperture 14. This subsequent motion closes the canister valve and terminates the dispensing cycle of the air freshener. The actuator cam 30 continues to complete the one-half rotation. As noted, the amount of rotation of the actuator cam 30 during each dispensing cycle is determined by the length of time that the controller 42 activates the motor 26. Should the actuator cam 30 not return to the off position shown in FIG. 2, the user upon replacing the cartridge 22 can manually return the cam to that position.

At the completion of the dispensing cycle, the motor is turned off and the use counter is incremented at step 90. The software timer is loaded with the dispense interval value at step 92 and begins decrementing to time another interval between dispensing operations. The program execution then enters the sleep state at step 94 during which power consumption is reduced by minimizing the functions that are active. The controller can awaken from the sleep state by either the reset switch 44 being pressed or upon expiration of the dispensing interval timer. Thus the control circuit 40 remains in the sleep state until the timer elapses at step 96 at which time the control program returns to step 60 to repeat the execution cycle.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. For example, although the present invention has been described in the context of an air freshener, it can be applied to dispensers for other types of aerosol substances, such as an insect repellant as one example. Accordingly, the scope of the invention should be determined from the following claims and not limited by the above disclosure.

What is claimed is:

1. An apparatus for periodically activating a control valve on a canister to discharge a quantity of the contents of the canister into a room, the apparatus comprising:
    an actuator which engages the canister to open the control valve;
    a sensor which senses a characteristic of the room and produces a signal indicating that characteristic;
    an input device which designates a dispense interval at which the contents of the canister are to be discharged into a room; and
    a controller connected to the sensor, the device and the actuator, and evaluating the signal from the sensor to determine whether the room is being used, the controller periodically activates the actuator at intervals which correspond to the dispense interval when a determination is made that the room is being used, and when a determination is made that the room is not being used the controller periodically activates the actuator at intervals which are longer than the dispense interval.

2. The apparatus as recited in claim 1 wherein the actuator comprises a motor, and a member connected to the motor which upon being driven by the motor engages the canister to open the control valve.

3. The apparatus as recited in claim 2 wherein the member is a cam with a lobe that engages the canister to operate the control valve.

4. The apparatus as recited in claim 1 wherein the sensor detects a level of light in the room, and the controller determines that the room is being used when the level of light exceeds a predefined threshold.

5. The apparatus as recited in claim 1 wherein the input device is a user operable switch having a plurality of positions corresponding to a plurality of dispense intervals.

6. The apparatus as recited in claim 1 wherein the controller further includes a counter which counts how many times the contents of the canister are discharged, and the controller providing an indication when the count exceeds a predetermined value.

7. The apparatus as recited in claim 1 wherein the controller is supplied by voltage from a battery, and further includes mechanism for detecting when the voltage is below a predefined magnitude and in response thereto providing an indication that the battery should be replaced.

8. The apparatus as recited in claim 1 further comprising a mode selector connected to the controller and selectively providing a signal to which the controller responds by periodically activating the actuator at intervals which correspond to the dispense interval regardless of any determination that the room is or is not being used.

9. An apparatus for periodically activating a control valve on a canister to discharge a quantity of the contents of the canister, the apparatus comprising:
    a housing for the canister;
    a motor within the housing;
    a member connected to the motor and when driven by the motor engages the canister to open the control valve;

a light sensor which produces a signal indicating a level of light outside the housing;

an input device by which a user designates a dispense interval at which the contents of the canister are to be discharged; and a controller connected to the sensor, the input device and the motor, the controller periodically activates the motor at intervals which correspond to the dispense interval when the level of light indicated by the sensor exceeds a predefined threshold, and when the level of light indicated by the sensor is less than the redefined threshold the controller periodically activates the motor at intervals which are longer than the dispense interval.

10. The apparatus as recited in claim 9 wherein the input device is a switch having a plurality of positions corresponding to a plurality of dispense intervals.

11. The apparatus as recited in claim 9 wherein the controller further includes a counter which counts how many times the contents of the canister are discharged, and the controller providing an indication when the count exceeds a predetermined value.

12. The apparatus as recited in claim 9 wherein the controller is supplied by voltage from a battery, and further includes mechanism for detecting when the voltage is below a predefined magnitude and in response thereto providing an indication that the battery should be replaced.

13. The apparatus as recited in claim 9 wherein the member is a cam with a lobe that engages the canister to operate the control valve.

14. The apparatus as recited in claim 9 wherein the member pushes the canister against the housing to operate the control valve.

15. The apparatus as recited in claim 9 further comprising a mode selector connected to the controller and selectively providing a signal to which the controller responds by periodically activating the motor at intervals which correspond to the dispense interval regardless of any determination that the room is or is not being used.

16. The apparatus as recited in claim 9 wherein the housing is adapted to be positioned against a wall.

* * * * *

UNITED STATES PATENT AND TRADEMARK OFFICE
CERTIFICATE OF CORRECTION

PATENT NO. : 6,644,507 B2  Page 1 of 1
APPLICATION NO. : 10/097879
DATED : November 11, 2003
INVENTOR(S) : Severine N. Borut et al.

It is certified that error appears in the above-identified patent and that said Letters Patent is hereby corrected as shown below:

Col. 6, line 46
 replace "bow"
 with --how--.

Col. 7, line 10
delete "when".

Col. 7, line 11
 replace "redefined"
 with --predefined--.

Signed and Sealed this

Second Day of January, 2007

JON W. DUDAS
*Director of the United States Patent and Trademark Office*